US00PP31703P2

(12) United States Plant Patent
Stewart et al.

(10) Patent No.: US PP31,703 P2
(45) Date of Patent: Apr. 28, 2020

(54) STRAWBERRY PLANT NAMED 'DRISSTRAWSIXTYSIX'

(50) Latin Name: ***Fragaria* x *ananassa***
Varietal Denomination: DrisStrawSixtySix

(71) Applicant: Driscoll's, Inc., Watsonville, CA (US)

(72) Inventors: Philip J. Stewart, Watsonville, CA (US); Renae R. Robertson, Watsonville, CA (US); Kevin Coons, Watsonville, CA (US); Joanne F. Coss, Watsonville, CA (US); Amy Marie Edmondson, Watsonville, CA (US); Agustin Renteria, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/350,432

(22) Filed: Nov. 14, 2018

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.

(Continued)

OTHER PUBLICATIONS

Fear et al., Unpublished U.S. Appl. No. 15/998,014, filed Jun. 11, 2018, titled "Strawberry Plant Variety Named 'DrisStrawFiftyEight'".
Ferguson et al. Unpublished U.S. Appl. No. 15/998,317, filed Aug. 3, 2018, titled "Strawberry Plant Variety Named 'DrisStrawSixty'".
Mendoza et al., Unpublished U.S. Appl. No. 16/350,139, filed Oct. 2, 2018, titled "Strawberry Plant Variety Named 'DrisStrawSixtySeven'".
Mendoza et al., Unpublished U.S. Appl. No. 15/998,020, filed Jun. 12, 2018, titled "Strawberry Plant Variety Named 'DrisStrawSixtyOne'".

(Continued)

*Primary Examiner* — Susan McCormick Ewoldt
(74) *Attorney, Agent, or Firm* — Morrison & Foerster LLP

(57) ABSTRACT

A new and distinct variety of strawberry plant named 'DrisStrawSixtySix', selected for its high yield, firm fruit, and compact plant type, is disclosed.

7 Drawing Sheets

(56) References Cited

U.S. PATENT DOCUMENTS

| | | | |
|---|---|---|---|
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| 2003/0079263 | P1 | 4/2003 | Gilford et al. |
| 2013/0276182 | P1 | 10/2013 | Fear et al. |

OTHER PUBLICATIONS

Mendoza et al., Unpublished U.S. Appl. No. 15/998,169, filed Jul. 12, 2018, titled "Strawberry Plant Variety Named 'DrisStrawSixtyThree'".

Mendoza et al., Unpublished U.S. Appl. No. 15/998,170, filed Jul. 12, 2018, titled "Strawberry Plant Variety Named 'DrisStrawSixtyTwo'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl. No. 15/998,031, filed Jun. 14, 2018, titled "Strawberry Plant Variety Named 'DrisStrawSixtyFour'".

STRAWBERRY PLANT NAMED 'DRISSTRAWSIXTYSIX'

Latin name:

Botanical classification: *Fragaria* x *ananassa.*

Varietal denomination: The varietal denomination of the claimed variety of strawberry plant is 'DrisStrawSixtySix'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSixtySix'.

Strawberry plant variety 'DrisStrawSixtySix' originated from a cross between the proprietary female parent 'DrisStrawFortyFour' (U.S. Plant Pat. No. 26,801) and the proprietary male parent '62R 83' (unpatented). Progeny plants from this cross, including 'DrisStrawSixtySix', were asexually propagated via stolons in Shasta County, Calif. in April of 2011. Strawberry plant variety 'DrisStrawSixtySix' was later specifically identified and selected in Monterey County, Calif. in May of 2012.

'DrisStrawSixtySix' was subsequently asexually propagated via stolons, and underwent further testing at a farm in Santa Barbara County, Calif. for six years (2012 to 2017). The present variety has been found to be stable and reproduce true to type through successive asexual propagations via stolons.

'DrisStrawSixtySix' exhibits the following distinguishing characteristics when grown under normal horticultural practices in Santa Barbara County, Calif.:

1. Spreading growth habit;
2. Inflorescence beneath foliage;
3. Calyx attachment inserted in fruit; and
4. Day neutral type of bearing.

'DrisStrawSixtySix' was selected for its high yield, firm fruit, and compact plant type.

DESCRIPTION OF THE DRAWINGS

This new strawberry plant is illustrated by the accompanying photographs which show fruit of the plant, as well as the flowers and leaves. The colors shown are as true as can be reasonably obtained by conventional photographic procedures. The photographs are of plants that are seven months old.

DESCRIPTION OF THE NEW VARIETY

Figure 1:
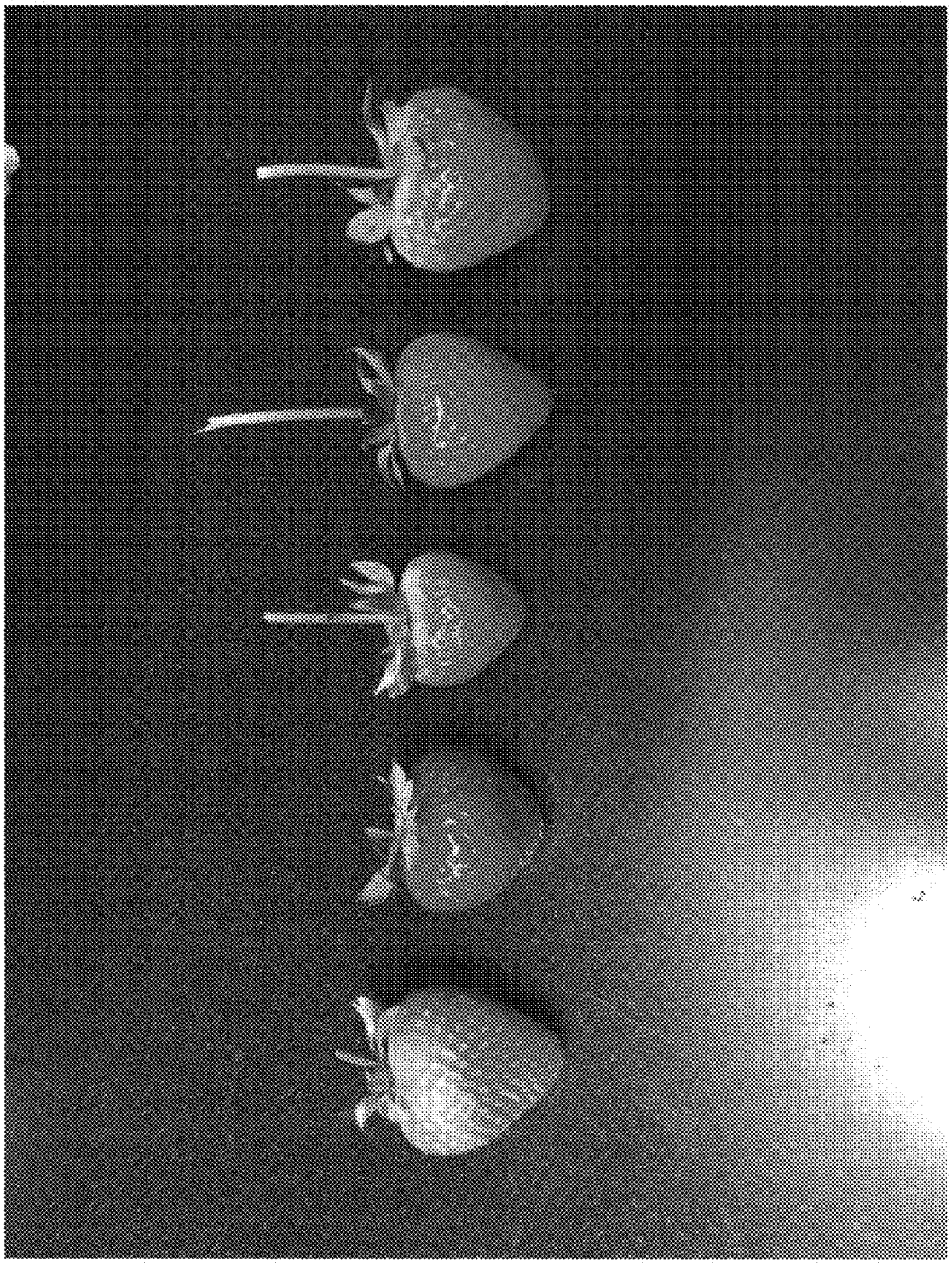
FIG. 1 illustrates whole fruit of variety 'DrisStrawSixtySix'.
Figure 2:
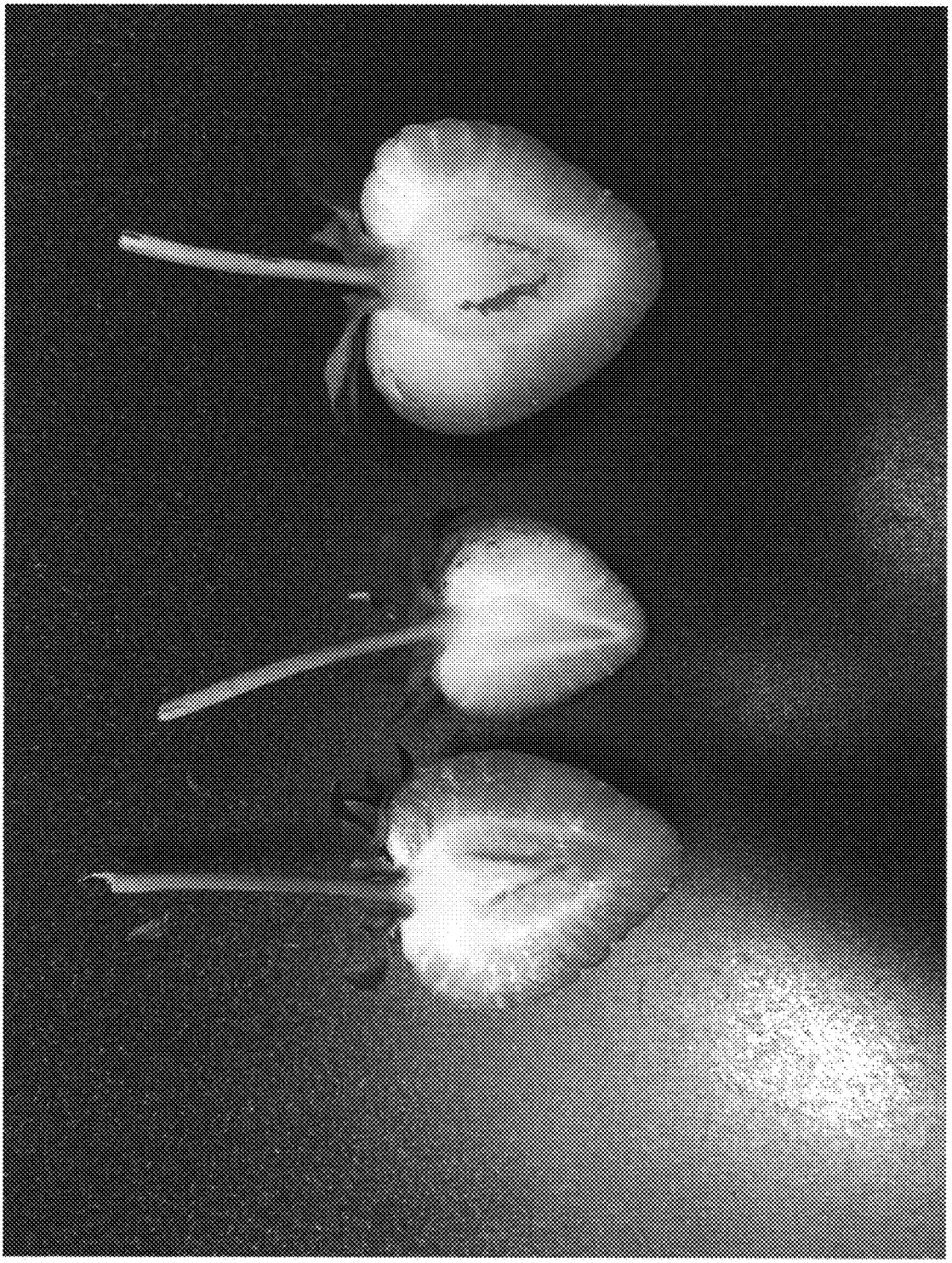
FIG. 2 illustrates longitudinal sections of fruit of variety 'DrisStrawSixtySix'.
Figure 3:
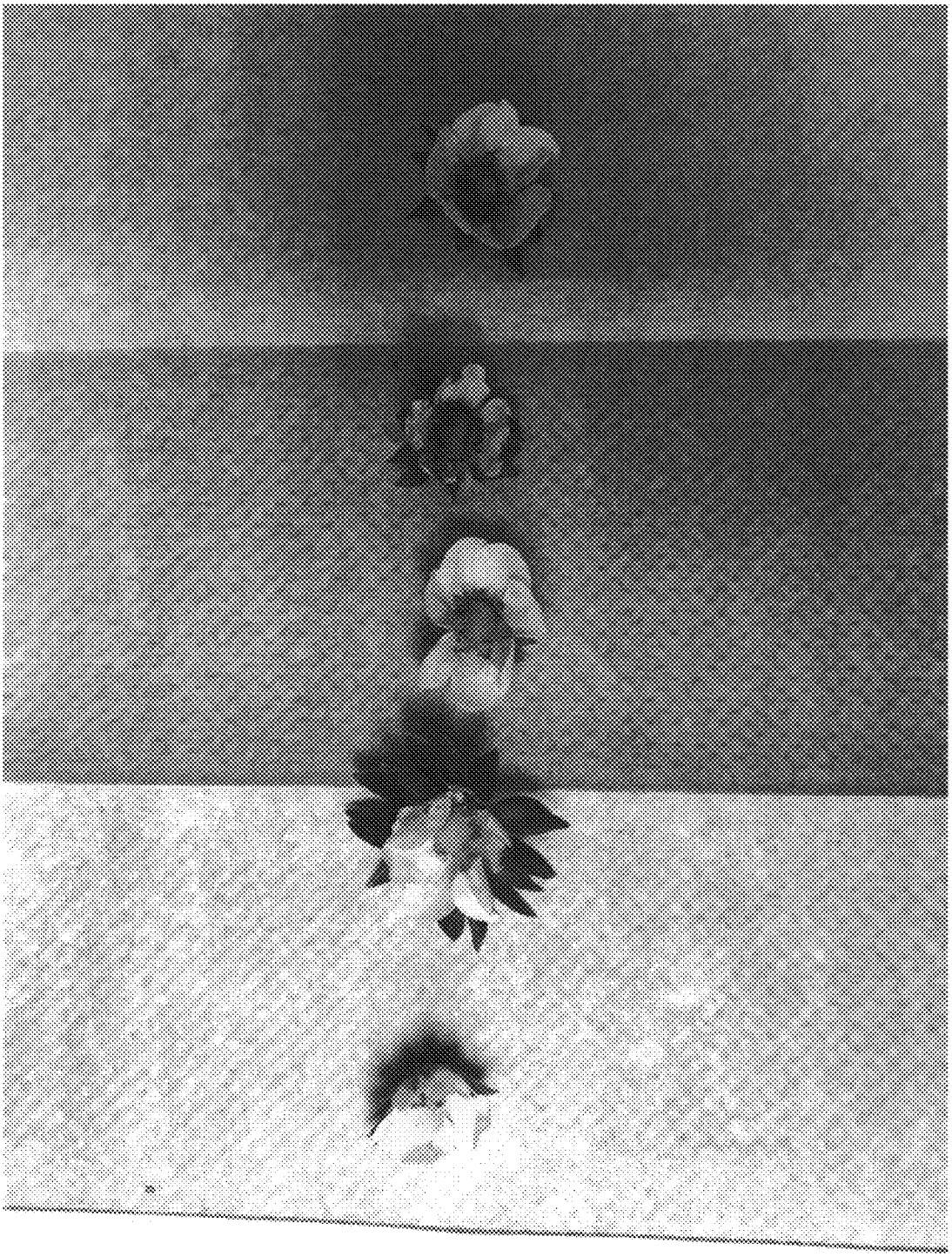
FIG. 3 illustrates the upper surfaces of flowers of variety 'DrisStrawSixtySix'.
Figure 4:
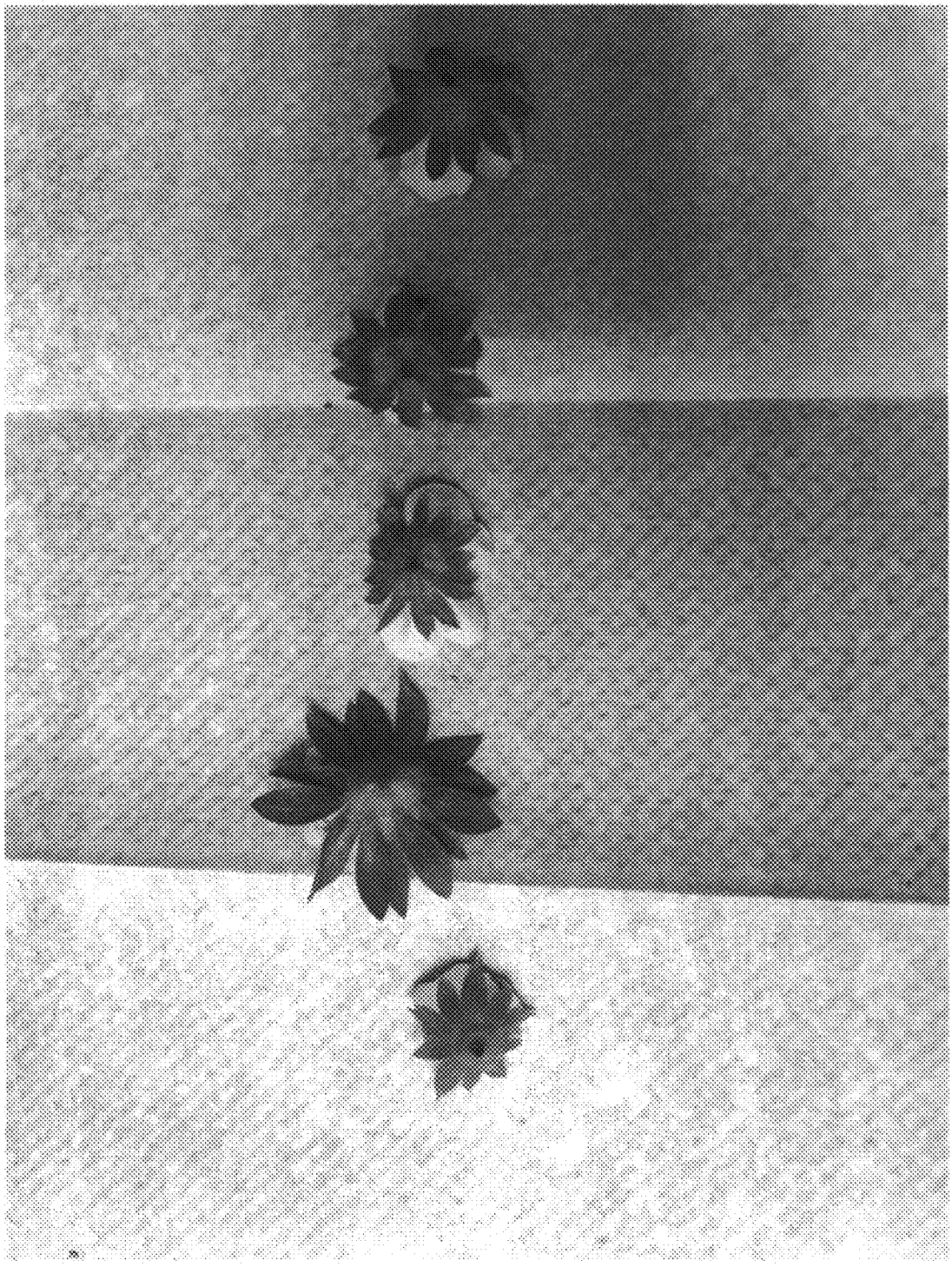
FIG. 4 illustrates the lower surfaces of flowers of variety 'DrisStrawSixtySix'.
Figure 5:
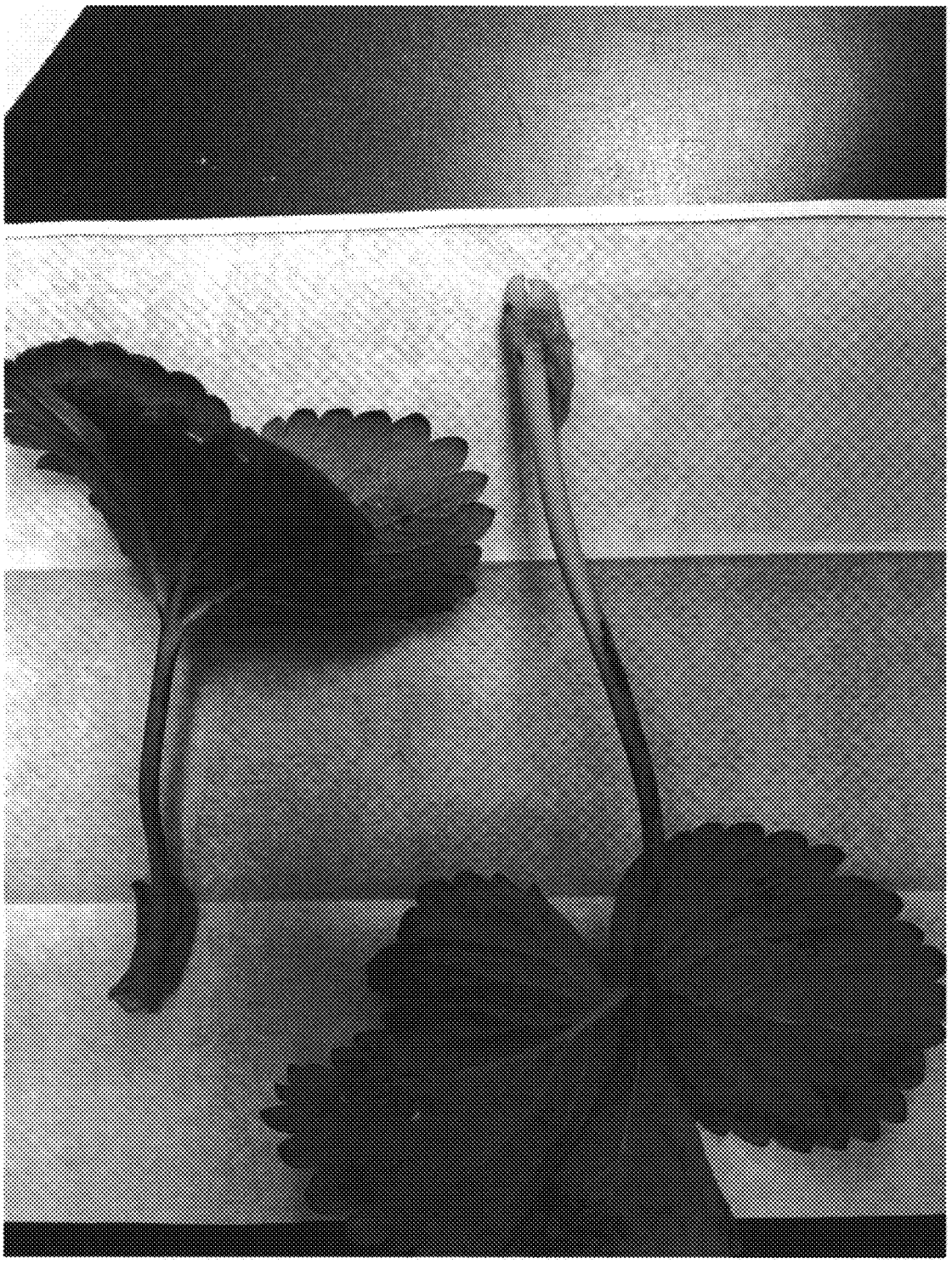
FIG. 5 illustrates leaves of variety 'DrisStrawSixtySix'.
Figure 6:
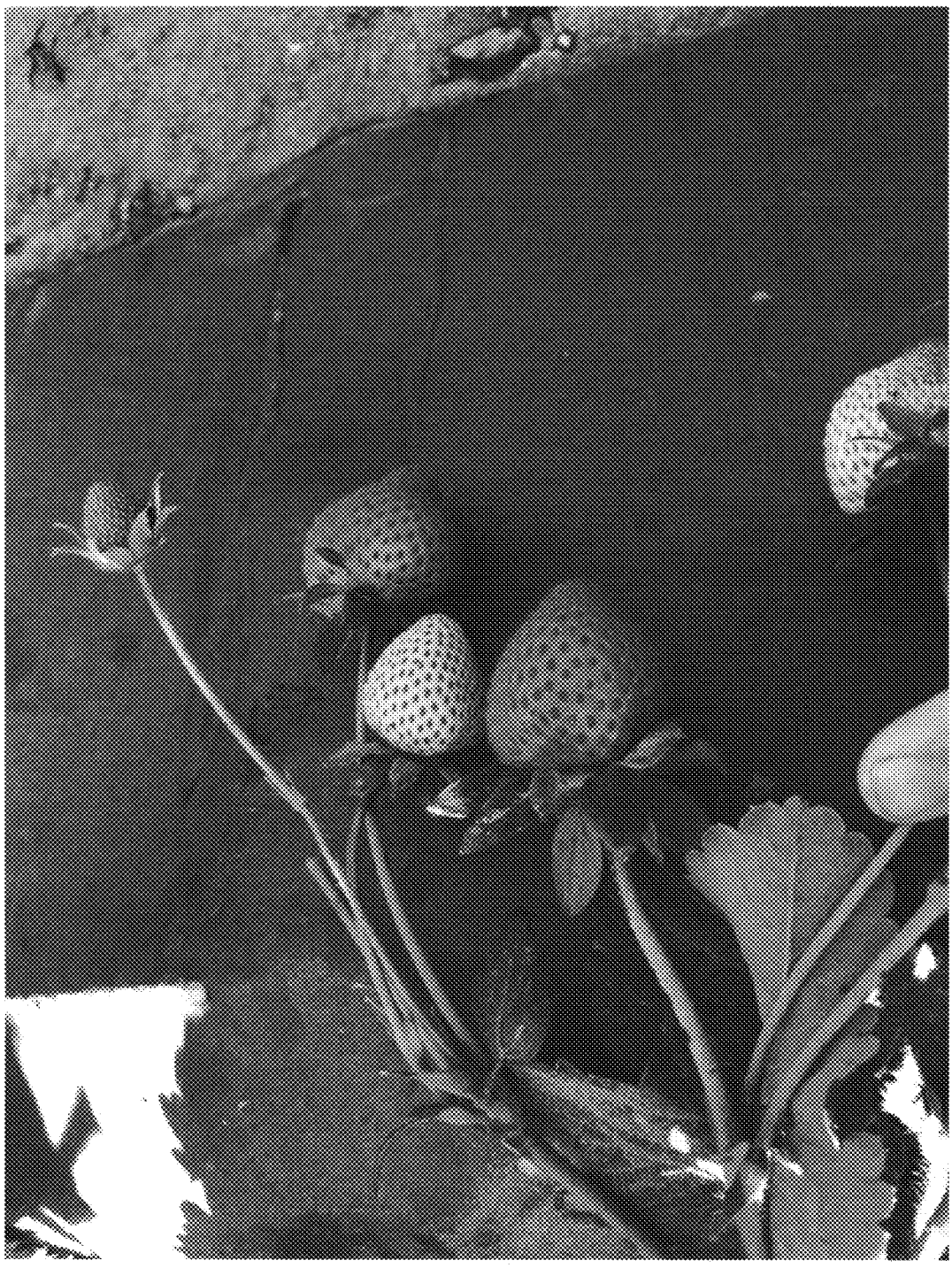
FIG. 6 illustrates fruit of variety 'DrisStrawSixtySix' at various stages of development.
Figure 7:
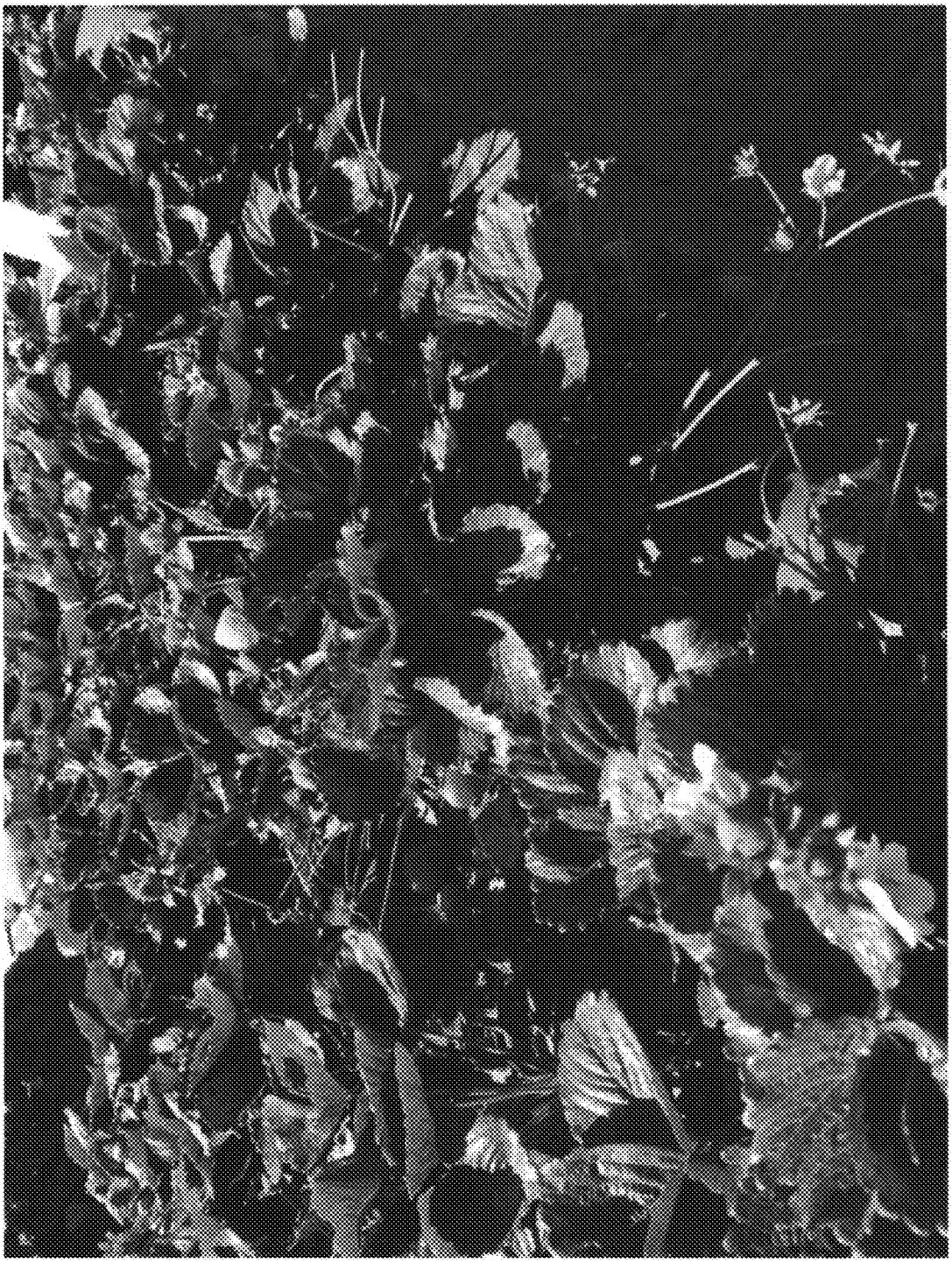
FIG. 7 illustrates plants of variety 'DrisStrawSixtySix'.

The following detailed descriptions set forth the distinctive characteristics of 'DrisStrawSixtySix'. The data which define these characteristics is based on observations taken in Santa Barbara County, Calif. from 2012 to 2017. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixtySix' has not been observed under all possible environmental conditions. The botanical description of 'DrisStrawSixtySix' was taken from plants that were seven months old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawSixtySix'.

Parentage:

*Female parent.*—The proprietary variety 'DrisStrawFortyFour' (U.S. Plant Pat. No. 26,801).

*Male parent.*—The proprietary variety '62R 83' (unpatented).

Plant:

*Height.*—14.9 cm.

*Diameter.*—28.3 cm.

*Number of crowns per plant.*—3.

*Growth habit.*—Spreading.

Stolon:

*Average number of daughter plants per square foot.*—14.

*Diameter at bract.*—2.60 mm.
*Anthocyanin coloration.*—Present.
*Stolon color with anthocyanin color present.*—RHS 162B (Moderate yellow).
*Length.*—42 cm.

Leaf:
*Number of leaflets.*—Three only.
*Color of upper surface.*—RHS 136A (Dark green).
*Color of lower surface.*—RHS 138B (Moderate yellow-green).
*Texture.*—Coriaceous.
*Vein color.*—RHS 138B (Moderate yellow-green).
*Venation pattern.*—Cross-venulate.
*Variegation.*—Absent.
*Terminal leaflets.*—Length: 5.9 cm. Width: 4.6 cm. Length/width ratio: 1.3. Number of teeth/terminal leaflet: 20. Shape of base: Rounded. Margin: Crenate. Shape in cross section: Concave.
*Petiole.*—Length: 9.4 cm. Diameter: 2.10 mm. Attitude of hairs: Horizontal. Bract frequency (number present on each petiole): 0. Color: RHS 138A (Moderate yellowish green).
*Petiolule.*—Length: 3.70 mm. Diameter: 2.00 mm.
*Stipule.*—Length: 2.5 cm. Width: 7.20 mm. Anthocyanin color: RHS 149A (Brilliant yellow-green).

Inflorescence:
*Position in relation to foliage.*—Beneath.
*Peduncle.*—Length: 17 cm. Diameter: 4 mm. Color: RHS 137D (Moderate yellowish green).
*Pedicel.*—Attitude of hairs: Upwards.
*Flower.*—Shape: Cyathiform. Flower diameter (petal tip to petal tip on non-flattened flower): 19.20 mm. Typical and observed number of flowers per plant: 5.60. Arrangement of petals: Overlapping. Stamen: Present.
*Petal.*—Length: 8.30 mm. Width: 7.90 mm. Length/width ratio: 1.1. Typical and observed petal number: 5. Color of upper side: RHS 155B (Yellowish white). Color of lower side: RHS 15513 (Yellowish white).
*Calyx.*—Diameter (sepal tip to sepal tip, measured on back of flower): 41.40 mm.
*Sepal.*—Length (sepal tip to point of attachment to receptacle): 12.50 mm. Width: 6.50 mm. Typical and observed sepal number: 11.
*Reproductive organs.*—Pistil: Pistil length: 1.0 mm. Pistil width: 0.2 mm. Pistil shape: Simple. Pistil color: RHS 154B (Brilliant yellow). Stamen: Stamen length: 1.0 mm. Stamen width: 0.5 mm. Stamen shape: Basifixed. Stamen color: RHS 154C (Brilliant yellow-green). Pollen: Pollen diameter: 0.1 mm. Pollen shape: Ovulate. Pollen color: RHS 12A (Vivid yellow).

Fruit:
*Length.*—38.80 mm.
*Width.*—35.50 mm.
*Length/width ratio.*—1.1.
*Fruit hollow length.*—17.40 mm.
*Fruit hollow width.*—10.10 mm.
*Fruit hollow length/width ratio.*—1.7.
*Weight.*—28.1 grams.
*Shape.*—Conical.
*Color.*—RHS 45A (Vivid red).
*Position of achenes.*—Level with surface.
*Position of calyx attachment.*—Inserted.
*Attitude of sepals.*—Outwards.
*Color of flesh (excluding core).*—RHS 44C (Vivid reddish orange).
*Color of core.*—RHS 39B (Deep yellowish pink).

Production:
*Flowering interval.*—February to September.
*Harvest interval.*—March to September.
*Type of bearing.*—Day neutral.
*Productivity.*—84,189 lbs to 110,387 lbs of fruit per acre per season from seven-month-old plants when grown in Santa Barbara County, Calif.

Resistance to abiotic stress and diseases:
*Drought.*—Moderately resistant.
*Heat.*—Moderately resistant.
*Botrytis fruit rot (botrytis cinerea).*—Moderately susceptible.
*Powdery mildew (podosphaera macularis).*—Moderately susceptible.
*Anthracnose crown rot (colletotrichum acutatum).*—Susceptible.

COMPARISON WITH PARENTAL AND COMMERCIAL VARIETIES

'DrisStrawSixtySix' differs from the proprietary female parent 'DrisStrawFortyFour' (U.S. Plant Pat. No. 26,801) in that 'DrisStrawSixtySix' is less vigorous but has increased fruit production and firmer fruit when compared with 'DrisStrawFortyFour'.

'DrisStrawSixtySix' differs from the proprietary male parent '62R 83' (unpatented) in that 'DrisStrawSixtySix' has increased fruit production and firmer fruit with fewer culls when compared with '62R 83'.

'DrisStrawSixtySix' differs from the commercial variety 'DrisStrawFortyFour' (U.S. Plant Pat. No. 26,801) in that plants of 'DrisStrawSixtySix' have a spreading growth habit, whereas plants of 'DrisStrawFortyFour' have a semi-upright growth habit. Further, plants of 'DrisStrawSixtySix' have inflorescence beneath foliage, whereas plants of 'DrisStrawFortyFour' have inflorescence above foliage. Moreover, plants of 'DrisStrawSixtySix' have a medium number of stolons, whereas plants of 'DrisStrawFortyFour' have many stolons. In addition, fruit of 'DrisStrawSixtySix' have a position of calyx attachment inserted in fruit, whereas fruit of 'DrisStrawFortyFour' have a position of calyx attachment level with fruit.

'DrisStrawSixtySix' differs from the commercial variety 'DrisStrawNine' (U.S. Plant Pat. No. 20,733) in that plants of 'DrisStrawSixtySix' have a spreading growth habit, whereas plants of 'DrisStrawNine' have an upright growth habit. Further, plants of 'DrisStrawSixtySix' have inflorescence beneath foliage, whereas plants of 'DrisStrawNine' have inflorescence above foliage. Moreover, fruit of 'DrisStrawSixtySix' have a position of calyx attachment inserted in fruit, whereas fruit of 'DrisStrawNine' calyx attachment level with fruit. In addition, plants of 'DrisStrawSixtySix' have a day neutral type of bearing, whereas plants of 'DrisStrawNine' have a fully remontant type of bearing.

We claim:

1. A new and distinct variety of strawberry plant named 'DrisStrawSixtySix' as shown and described herein.

* * * * *